United States Patent [19]

Murayama et al.

[11] 3,975,462
[45] Aug. 17, 1976

[54] PIPERIDINE-SPIRO-HYDANTOIN DERIVATIVES AND THEIR USE AS STABILIZERS

[75] Inventors: Keisuke Murayama; Syoji Morimura; Takao Yoshioka; Toshimasa Toda; Eiko Mori; Hideo Horiuchi; Susumu Higashida; Katsuaki Matsui; Tomoyuki Kurumada; Noriyuki Ohta; Hisayou Ohsawa, all of Hiro, Japan

[73] Assignee: Sankyo Company Limited, Tokyo, Japan

[22] Filed: Oct. 22, 1974

[21] Appl. No.: 517,008

Related U.S. Application Data

[63] Continuation-in-part of Ser. No. 366,575, June 4, 1973, abandoned, which is a continuation of Ser. No. 265,313, June 22, 1972, abandoned.

[30] Foreign Application Priority Data

July 2, 1971   Japan.................................. 46-48646

[52] U.S. Cl....................... 260/880 R; 260/45.8 NE; 260/45.8 NT
[51] Int. Cl.²...................... C08K 5/34; C08K 5/51
[58] Field of Search................ 260/45.8 N, 45.8 NT, 260/45.8 NZ, 309.5

[56] References Cited
UNITED STATES PATENTS

| | | | |
|---|---|---|---|
| 2,143,816 | 1/1939 | Jacobson | 260/309.5 |
| 2,225,384 | 12/1940 | Graenacher et al. | 260/309.5 |
| 2,551,134 | 5/1951 | Jennings | 260/309.5 |
| 2,687,416 | 8/1954 | Persch et al. | 260/309.5 |
| 2,778,825 | 1/1957 | Melamed | 260/244 |
| 2,928,841 | 3/1960 | McConnell et al. | 260/309.5 |
| 3,213,104 | 10/1965 | Cashin et al. | 260/309.5 |
| 3,542,729 | 11/1970 | Murayama et al. | 260/45.8 |
| 3,705,126 | 12/1972 | Matsui et al. | 260/45.8 |

*Primary Examiner*—Lewis T. Jacobs
*Assistant Examiner*—R. A. White
*Attorney, Agent, or Firm*—Toren, McGeady and Stanger

[57] ABSTRACT

Piperidine-spiro-hydantoin derivatives having the formula

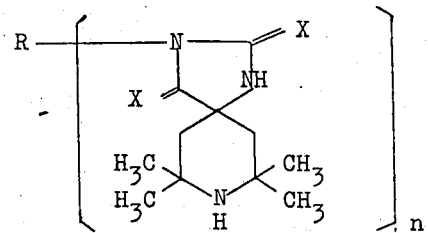

(I)

wherein X represents oxygen atom or sulfur atom; $n$ is an integer of 1 to 4 inclusive, and R represents various aliphatic or aromatic groups depending on the value of $n$.

These compounds (I) are useful as stabilizers against photo and thermal deterioration of various synthetic polymers and can be prepared, for example, by reacting the corresponding 3-unsubstituted piperidine-spiro-hydantoin compound with the halide $R-(X_1)_n$ in which R and $n$ are as defined herein and $X_1$ is a halogen atom.

16 Claims, No Drawings

PIPERIDINE-SPIRO-HYDANTOIN DERIVATIVES AND THEIR USE AS STABILIZERS

CROSS-REFERENCE TO PRIOR APPLICATIONS:

This is a Continuation-in-Part of Ser. No. 366,575 of June 4, 1973, now abandoned, which in turn was a Continuation of Ser. No. 265,313 of June 22, 1972, now abandoned.

This invention relates to a new group of piperidine-spiro-hydantoin derivatives and their use as stabilizers.

More particularly, this invention is concerned with piperidine-spiro-hydantoin derivatives having the formula

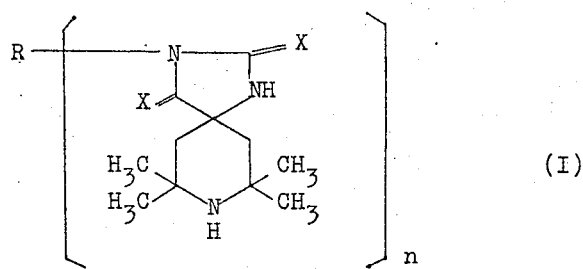

In the above formula (I), X represents oxygen atom or sulfur atom: $n$ is an integer of 1 to 4 inclusive; and R represnts, when $n$ is 1, an alkenyl group which may be substituted with halongen, an alkynyl group which may be substituted with phenyl, an aralkyl group which may be substituted with halogen, alkyl of 1 to 4 carbon atoms or halomethyl, a hydroxyalkyl group, an alkoxyalkyl group, an alkenyloxyalkyl group, an aryloxyalkyl group, an alkylthioalkyl group, an acyloxyalkyl group, an epoxyalkyl group, an N-alkyl-substituted aminoalkyl group, an alkoxycarbonylalkyl group, an aryloxycarbonylalkyl group, an aliphatic acyl group, an alkoxycarbonyl group, a phosphino group which is substituted with phenoxy or alkoxy or a phosphinyl group which is substituted with phenoxy or alkoxy, when $n$ is 2, an alkenylene group of 4 to 18 carbon atoms, a dialkyleneether group, an aralkylene group, a bis(acyloxyalkylene) group or an alkylene-bis(oxycarbonylalkyl) group, when $n$ is 3, a tris(acyloxyalkylene) group, an alkanetris(oxycarbonylalkyl) group or a group of the formula

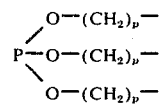

in which $p$ is an integer of 1 to 8 inclusive and $p$'s may be the same or different, and, when $n$ is 4, a tetrakis(acyloxyalkylene) group.

This invention is also concerned with stabilization of synthetic polymers against photo-and thermal-deteriorations thereof by having incorporated therein, in a sufficient amount to prevent said deterioration at least one of the piperidine-spiro-hydantoin derivatives (I).

The term "synthetic polymer" as used herein are intended to embrace polyolefins including homopolymers of olefins such as low-density and high-density polyethylene, polypropylene, polystyrene, polybutadiene, polyisoprene and the like, and copolymers of olefins with other ethylenically unsaturated monomers such as ethylene-propylene copolymer, ethylene-butene copolymer, ethylene-vinyl acetate copolymer, styrene-butadiene copolymer, acrylonitrile-styrene-butadiene copolymer and the like;

polyvinyl chlorides and polyvinylidene chlorides including homopolymer of each of vinyl chloride and vinylidene chloride, vinyl chloride-vinylidene chloride copolymer and copolymers of each of vinyl chloride and vinylidene chloride with vinyl acetate or other ethylenically unsaturated monomers;

polyacetals such as polyoxymethylene and polyoxyethylene; polyesters such as polyethylene terephthalate; polyamides such as 6-nylon, 6,6-nylon and 6,10-nylon; and polyurethanes.

In the above formula (I), R may be exemplified, for instance, by the following groups:

When $n$ is 1, there may be mentioned alkenyl groups which may be substituted with halogen, e.g., allyl, cis- or trans-2-butenyl, 2-methylallyl or trans-3-bromoallyl; alkynyl groups which may be substituted with phenyl, e.g., 2-propynyl or 3-phenyl-2-propynyl; aralkyl groups which may be substituted with halogen, alkyl of 1 - 4 carbon atoms or halomethyl, e.g., benzyl, phenethyl, p-chlorobenzyl, p-methylbenzyl, or p-chloromethylbenzyl; hydroxyalkyl groups, e.g., 2-hydroxyethyl, 3-hydroxypropyl or 4-hydroxybutyl; alkoxyalkyl groups, e.g., methoxymethyl or ethoxymethyl; alkenyloxyalkyl groups, e.g., 2-vinyloxyethyl; aryloxyalkyl groups, e.g., 2-phenoxyethyl; alkylthioalkyl groups, e.g., 2-methylthioethyl; acyloxyalkyl groups such as alkanoyloxyalkyl groups, e.g., 2-acetoxyethyl or 4-decanoyloxybutyl, alkenoyloxyalkyl groups, e.g., 2-acryloyloxyethyl or 2-methacryloyloxyethyl, or aroyloxyalkyl group, e.g., 2-benzoyloxyethyl or 2-m-toluoyloxyethyl; epoxyalkyl groups, e.g., 2,3-epoxypropyl; N-alkylsubstituted aminoalkyl groups, e.g., 2-dimethylaminoethyl; alkoxycarbonylalkyl groups, e.g., ethoxycarbonylmethyl; aryloxycarbonylalkyl groups, e.g., phenoxycarbonylmethyl; aliphatic acyl groups, e.g., acetyl, propionyl or butyryl; alkoxycarbonyl groups, e.g., ethoxycarbonyl; phosphino groups which are substituted with phenoxy or alkoxy, e.g., $(C_2H_5O)_2-P-$ or

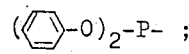

and phosphinyl groups which are substituted with phenoxy or alkoxy, e.g.,

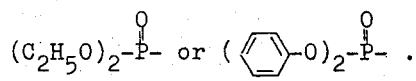

When $n$ is 2, R may be alkenylene groups, e.g., —CH$_2$—CH=CH—CH$_2$—; dialkyleneether groups, e.g., —(CH$_2$)$_2$—O—(CH$_2$)$_2$— aralkylene groups, e.g.,

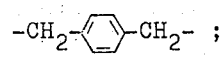

bis(acyloxyalkylene) groups, such as bis(alkanoyloxyalkylene) groups, e.g., —(CH$_2$)$_2$—O—CO—CO—O—(CH$_2$)$_2$— , —(CH$_2$)$_2$—O—CO—(CH$_2$)$_2$—CO—O—(CH$_2$)$_2$— or —(CH$_2$)$_2$—O—CO—(CH$_2$)$_4$—CO—O—(CH$_2$)$_2$— or bis(aroyloxyalkylene) groups, e.g.,

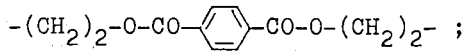

and alkylenebis(oxycarbonylalkyl) groups, e.g., —CH$_2$—CO—O—(CH$_2$)$_2$—O—CO—CH$_2$—.

When n is 3, R may be tris(acyloxyalkylene) groups, such as tris(alkanoyloxyalkylene) groups, e.g.,

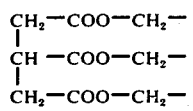

or tris(aroyloxyalkylene) groups, e.g.,

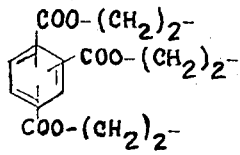

and the group of the formula

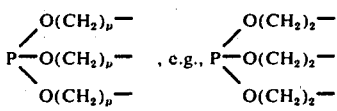

When n is 4, R may be tetrakis(acyloxyalkylene) groups, such as tetrakis(aroyloxyalkylene) groups, e.g.,

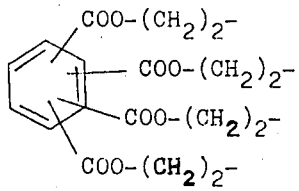

Synthetic polymers have been widely utilized in the art, in view of their excellent properties, in various forms or shapes, for example, filament, fibre, yarn, film, sheet, other molded article, latex and foam. However, these polymers have some drawbacks such as poor light- and heat-stabilities and the like. Stated illustratively, polyolefins and polyurethane elastomers frequently tend to undergo severe deterioration when exposed to light such as sunlight or ultraviolet ray, and polyvinyl chloride and polyvinylidene chloride frequently tend to deteriorate and become colored by the action of light and heat together with elimination of hydrogen chloride therefrom. Polyamides are also frequently subjected to photo-deterioration. For the purpose of stabilizing these synthetic polymers against such deterioration, there have heretofore been proposed in the art a number of stabilizers; for example, for polyolefins, benzotriazole compounds and benzophenone compounds; for polyurethanes, phenol compounds and benzophenone compounds; and for polyvinyl chloride and polyvinylidine chloride, lead salts such as basic lead silicate and tribasic lead maleate, and organotin compounds such as dibutyltin laurate and dibutyltin maleate.

Although such prior stabilizers are known to be considerably satisfactory, there still remained some problems to be improved.

Thus, numerous attempts have been made in the art to find and develop new and more effective stabilizers.

As a result of our extensive studies, it has now been found that the piperidine-spiro-hydantoin derivatives (I) of this invention can be satisfactorily prepared and exhibit a high stabilizing effect against photo- and thermal-deterioration of the synthetic polymers.

It is, accordingly, an object of this invention to provide new and useful piperidine-spiro-hydantoin derivatives (I).

Another object is to provide synthetic polymer composition stabilized against photo- and thermal-deterioration thereof by having incorporated therein, in a sufficient amount to prevent the deterioration, at least one of the piperidine-spiro-hydantoin derivatives (I).

Other objects of this invention will become apparent to those skilled in the art from the following description.

In one aspect of this invention, the piperidine-spiro-hydantoin derivatives (I) are all new substances unknown in the art.

Among the piperidine-spiro-hydantoin derivatives (I) of this invention, particularly useful are the piperidine-spiro-hydantoin derivatives having the formula (I) wherein n is 1 and R is an alkenyl group, an alkoxyalkyl group, an acyloxyalkyl group, an epoxyalkyl group, an alkoxycarbonylalkyl group or diphenoxyphosphin group, and wherein the alkyl moiety of the above-listed groups that is directly attached to the N atom of 3-position of a piperidine-spiro-hydantoin structure has 1 to 8 carbon atoms.

More specifically, a most preferable group of the piperidine-spiro-hydantoin derivatives (I) of this invention can be represented by the formula (II)

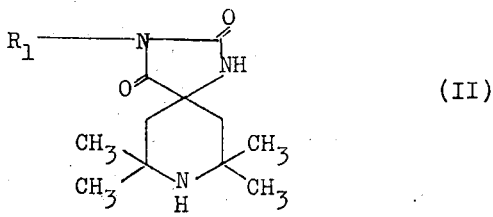

wherein R$_1$ is allyl group, an alkoxyalkyl group, an alkanoyloxyalkyl group, an alkenoyloxyalkyl group or 2,3-epoxypropyl group and the alkyl moiety, attached directly to the N atom of 3-position of a piperidine-spiro-hydantoin structure, of the above-listed groups has 1 to 4 carbon atoms.

Among the piperidine-spiro-hydantoin derivative (II), highly superior stabilizing effect against photo-deterioration of synthetic polymers as well as good compatibility with the polymers to be stabilized can be attained with those compounds of the above formula (II) wherein R$_1$ is allyl group, an alkoxyalkyl group, an alkanoyloxyalkyl group or alkenoyloxyalkyl group. The compounds of the above formula (II) wherein R$_1$ is 2,3-epoxypropyl group are found to have high stabilizing effect against thermal-deterioration, together with good stabilization against photo-deterioration.

Representatives of the piperidine-spiro-hydantoin derivatives (I) of this invention are illustrated hereinbelow. Such illustration, however, should not be construed to be limiting the scope of this invention.

1. 3-allyl-1,3,8-triaza-7,7,9,9-tetramethyl-spiro[4.5]-decane-2,4-dione
2. 3-allyl-1,3,8-triaza-7,7,9,9-tetramethyl-spiro[4.5]-decane-2,4-dithione
3. 1,3,8-triaza-3-(trans-2-butenyl)-7,7,9,9-tetramethyl-spiro[4.5]decane-2,4-dione
4. 1,3,8-triaza-3-(trans-3-bromoallyl)-7,7,9,9-tetramethyl-spiro[4.5]decane-2,4-dione
5. 1,3,8-triaza-7,7,9,9-tetramethyl-3-(2-methylallyl)-spiro-[4.5]decane-2,4-dione
6. 1,3,8-triaza-7,7,9,9-tetramethyl-3-(2-propynyl)-spiro-[4.5]decane-2,4-dione
7. 1,3,8-triaza-7,7,9,9-tetramethyl-3-(3-phenyl-2-propynyl)-spiro[4.5]decane-2,4-dione
8. 1,3,8-triaza-3-benzyl-7,7,9,9-tetramethyl-spiro[4.5]-decane-2,4-dione
9. 1,3,8-triaza-3-(p-chlorobenzyl)-7,7,9,9-tetramethyl-spiro[4.5]decane-2,4-dione
10. 1,3,8-triaza-7,7,9,9-tetramethyl-3-(p-methylbenzyl)-spiro[4.5]decane-2,4-dione
11. 1,3,8-triaza-3-(p-chloromethylbenzyl)-7,7,9,9-tetramethyl-spiro[4.5]decane-2,4-dione
12. 1,3,8-triaza-7,7,9,9-tetramethyl-3-phenethyl-spiro[4.5]decane-2,4-dione
13. 1,3,8-triaza-3-(2-hydroxyethyl)-7,7,9,9-tetramethyl-spiro[4.5]decane-2,4-dione
14. 1,3,8-triaza-3-(3-hydroxypropyl)-7,7,9,9-tetramethyl-spiro[4.5]decane-2,4-dione
15. 1,3,8-triaza-3-(4-hydroxybutyl)-7,7,9,9-tetramethyl-spiro[4.5]decane-2,4-dione
16. 1,3,8-triaza-7,7,9,9-tetramethyl-3-methoxymethyl-spiro[4.5]decane-2,4-dione
17. 1,3,8-triaza-3-ethoxymethyl-7,7,9,9-tetramethyl-spiro[4.5]decane-2,4-dione
18. 1,3,8-triaza-7,7,9,9-tetramethyl-3-(2-vinyloxyethyl)-spiro[4.5]decane-2,4-dione
19. 1,3,8-triaza-7,7,9,9-tetramethyl-3-(2-phenoxyethyl)-spiro[4.5]decane-2,4-dione
20. 1,3,8-triaza-7,7,9,9-tetramethyl-3-(2-methylthioethyl)-spiro[4.5]decane-2,4-dione
21. 3-(2-acetoxyethyl)-1,3,8-triaza-7,7,9,9-tetramethyl-spiro[4.5]decane-2,4-dione
22. 1,3,8-triaza-3-(4-decanoyloxybutyl)-7,7,9,9-tetramethyl-spiro[4.5]decane-2,4-dione
23. 3-(2-acryloyloxyethyl)-1,3,8-triaza-7,7,9,9-tetramethyl-spiro[4.5]decane-2,4-dione
24. 1,3,8-triaza-3-(2-benzoyloxyethyl)-7,7,9,9-tetramethyl-spiro[4.5]decane-2,4-dione
25. 1,3,8-triaza-7,7,9,9-tetramethyl-3-(2-m-toluoyloxyethyl)-spiro[4.5]decane-2,4-dione
26. 1,3,8-triaza-7,7,9,9-tetramethyl-3-(2-dimethylaminoethyl)-spiro[4.5]decane-2,4-dithione
27. 1,3,8-triaza-3-(2,3-epoxypropyl)-7,7,9,9-tetramethyl-spiro[4.5]decane-2,4-dione
28. 1,3,8-triaza-3-ethoxycarbonylmethyl-7,7,9,9-tetramethyl-spiro[4.5]decane-2,4-dione
29. 1,3,8-triaza-7,7,9,9-tetramethyl-3-phenoxycarbonylmethyl-spiro[4.5]decane-2,4-dione
30. 1,3,8-triaza-3-ethoxycarbonyl-7,7,9,9-tetramethyl-spiro [4.5]decane-2,4-dione
31. 3-acetyl-1,3,8-triaza-7,7,9,9-tetramethyl-spiro[4.5]decane-2,4-dione
32. 1,3,8-triaza-7,7,9,9-tetramethyl-3-diphenoxyphosphino-spiro[4.5]decane-2,4-dithione
33. 1,3,8-triaza-7,7,9,9-tetramethyl-3-diphenoxyphosphinyl-spiro[4.5]decane-2,4-dithione
34. 1,4-bis(1,3,8-triaza-7,7,9,9-tetramethyl-2,4-dioxo-spiro[4.5]-3-decyl)-trans-2-butene
35. 2,2'-bis(1,3,8-triaza-7,7,9,9-tetramethyl-2,4-dioxo-spiro[4.5]-3-decyl)diethylether
36. $\alpha$, $\alpha'$-bis(1,3,8-triaza-7,7,9,9-tetramethyl-2,4-dioxo-spiro[4.5]-3-decyl)-p-xylene
37. bis[2-(1,3,8-triaza-7,7,9,9-tetramethyl-2,4-dioxo-spiro[4.5]-3-decyl)ethyl]succinate
38. bis[2-(1,3,8-triaza-7,7,9,9-tetramethyl-2,4-dioxo-spiro[4.5]-3-decyl)ethyl]adipate
39. bis[2-(1,3,8-triaza-7,7,9,9-tetramethyl-2,4-dioxo-spiro[4.5]-3-decyl)ethyl]terephthalate
40. ethyleneglycol bis(1,3,8-triaza-7,7,9,9-tetramethyl-2,4-dioxo-spiro[4.5]-3-decylmethylcarboxylate)
41. tris[2-(1,3,8-triaza-7,7,9,9-tetramethyl-2,4-dioxo-spiro[4.5]-3-decyl)ethyl]tricarballylate
42. tris[2-(1,3,8-triaza-7,7,9,9-tetramethyl-2,4-dioxo-spiro[4.5]-3-decyl)ethyl]trimellitate
43. tris(1,3,8-triaza-7,7,9,9-tetramethyl-2,4-dioxo-spiro[4.5]-3-decyl) acetin
44. 2,2',2''-tris(1,3,8-triaza-7,7,9,9-tetramethyl-2,4-dithioxo-spiro[4.5]-3-decyl) triethylphosphite
45. tetrakis[2-(1,3,8-triaza-7,7,9,9-tetramethyl-2,4-dioxo-spiro[4.5]-3-decyl)ethyl]pyromellitate For the most preferable and practical results, the following compounds may be listed:

3-Allyl-1,3,8-triaza-7,7,9,9-tetramethyl-spiro[4.5]decane-2,4-dione,
1,3,8-triaza-3-ethoxymethyl-7,7,9,9-tetramethyl-spiro[4.5]decane-2,4-dione,
3-(2-acetoxyethyl)-1,3,8-triaza-7,7,9,9-tetramethyl-spiro[4.5]decane-2,4-dione,
1,3,8-triaza-3-(4-decanoyloxybutyl)-7,7,9,9-tetramethyl-spiro[4.5]decane-2,4-dione,
3-(2-acryloyloxyethyl)-1,3,8-triaza-7,7,9,9-tetramethyl-spiro[4.5]decane-2,4-dione and
1,3,8-triaza-3-(2,3-epoxypropyl)-7,7,9,9-tetramethyl-spiro[4.5]decane-2,4-dione.

The piperidine-spiro-hydantoin derivatives (I) of this invention can be easily prepared, for instance, by the reaction of a compound having the following formula (III) or an alkali metal salt thereof with a halide having the formula [R-$(X_1)_n$] as shown in the following reaction schema:

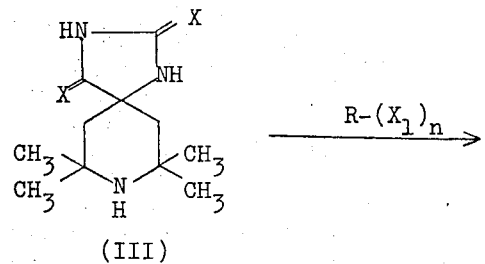

(III)

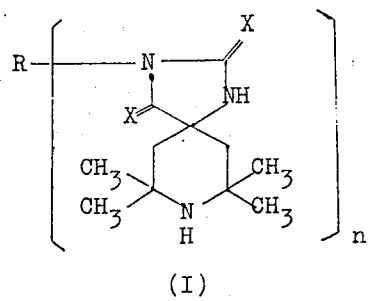

(I)

In the above formulae, $n$, R and X are as defined above and $X_1$ is a halogen atom.

In carrying out the above-exemplified process for the preparation of the piperidine-spiro-hydantoin derivative (I), the reaction may be effected by adding a stoichiometric amount of the halide $[R—(X_1)_n]$ to the starting compound (III), optionally dissolved or suspended in water or a suitable organic solvent, e.g., benzene, toluene, xylene, dimethylformamide and the like, and either standing the resulting mixture at room temperature or heating the mixture under reflux. Where the starting compound (III) is of a free base form, the reaction may be satisfactorily effected in the presence of an inorganic or organic base which acts as an acid-binding agent, e.g., alkali metal carbonate or tertiary amine. Where the starting compound (III) is of an alkali metal salt form, the reaction may be smoothly effected in the absence of the acid-binding agent.

The starting compound of the formula (III) wherein X is sulfur atom is new substance and it may be readily prepared by reacting 4-amino-4-cyano-2,2,6,6-tetramethylpiperidine with carbon disulfide and sulfur in the presence of a suitable oraganic solvent at room temperature.

In still another aspect of this invention, there is provided a synthetic polymer composition stabilized against photo- and thermal-deteriorations, which contains at least one of the new piperidine-spiro-hydantoin derivatives (I) having incorporated therein.

The piperidine-spiro-hydantoin derivatives (I) employed as a stabilizer in the present invention may be readily incorporated into the synthetic polymers by any of the various standard procedures commonly utilized in the art. The stabilizer may be incorporated into the synthetic polymers at any desired stage prior to the manufacture of shaped articles therefrom. Thus, for example, the stabilizer in the form of a dry powder may be admixed with the synthetic polymer, or a suspension or emulsion of the stabilizer may be admixed with a solution, suspension or emulsion of the synthetic polymer.

The amount of the piperidine-spiro-hydantoin derivatives (I) employed in the synthetic polymer in accordance with the present invention may be varied widely, depending upon the types, properties and particular uses of the synthetic polymer to be stabilized. In general, the piperidine-spiro-hydantoin derivatives of the formula (I) may be added in an amount ranging from 0.01 to 5.0% by weight, based on the amount of the synthetic polymer, but the practical range is varied depending upon the type of the synthetic polymer, that is 0.01 to 2.0% by weight, preferably 0.02 to 1.0% by weight for polyolefins, 0.01 to 1.0% by weight, preferably 0.02 to 0.5% by weight for polyvinyl chloride and polyvinylidene chloride, and 0.01 to 5.0% by weight, preferably 0.02 to 2.0% by weight for polyurethanes and polyamides.

The present stabilizer may be used alone or in combination with other known antioxidants, ultraviolet absorbents, fillers, pigments and the like. Examples of the antioxidants which may be utilized include 2,6-di-tert-.butyl-p-cresol, 4,4′-thio-bis(3-methyl-6-tert.butylphenol), 4,4′-butylidene-bis(3-methyl-6-tert.butylphenol), tris(2-methyl-4-hydroxy-5-tert.butylphenyl)butane, tetrakis[β-(3,5-di-tert.butyl-4-hydroxyphenyl)propoxymethyl]methane, triphenyl phosphite, dilauryl thiodipropionate and the like. Examples of the ultraviolet absorbents which may be employed include 4-tert.butylphenyl salicylate, 2-hydroxy-4-octoxybenzophenone, 2-(2′-hydroxy-3′,5′-di-tert.butylphenyl)-5-chloro-benzotriazole, methyl α-cyano-β-methyl-β-(p-methoxyphenyl)acrylate, nickel (II) salt of [2,2′-thiobis(4-tert.butylphenolate)]-n-butylamine and the like. The additives as set forth above, when employed, may be blended into a synthetic polymer composition, usually in a ratio of about 0.5 – 3.0 to 1 of the piperidine-spiro-hydantoin derivative (I) of this invention.

If desired, two or more of the present stabilizers i.e. the piperidine-spiro-hydantoin derivatives of the formula (I) may also be satisfactorily used in this invention.

In order that the invention may be better understood, the following Examples are given solely for the purpose of illustration of this invention. In the Examples, all part are given by weight unless otherwise indicated and the number of the compound as used hereinbelow is the same as illustratively shown above.

Example 1 and 2 describe the preparation of the piperidine-spiro-hydantoin derivatives (I) of this invention.

Example 3 through 10 describe synthetic polymer compositions having incorporated therein an effective amount of the present piperidine-spiro-hydantoin derivative (I), together with their stabilizing effects against photo- and thermal-deteriorations.

EXAMPLE 1

1,3,8-Triaza-7,7,9,9-tetramethyl-3-(2-propynyl)-spiro[4.5]decane-2,4-dione

To a mixture of 2.6 g. of potassium salt of 1,3,8-triaza-7,7,9,9-tetramethyl-spiro[4.5]decane-2,4-dione and 1.2 g. of 2-propynyl bromide was added 10 ml. of dimethylformamide and the resulting mixture was heated at 60° – 70°C. for 5 hours. After completion of the reaction, the reaction mixture was concentrated and the residue was dissolved in benzene. The benzene solution was concentrated and the crystalline substance thus separated was recrystallized from aqueous ethanol to give the desired product as white crystals melting at 156° – 157°C.

Analysis for $C_{14}H_{21}N_3O_2$: Calculated: C, 63.85%; H, 8.04%; N, 15.96%. Found: C, 63.77%; H, 7.96%; N, 15.94%.

IR spectrum (Nujol mull): $\nu_{NH}$ 3390 cm$^{-1}$, $\nu_{C≡C}$ 2120 cm$^{-1}$, $\nu_{C-O}$ 1775, 1720 cm$^{-1}$.

EXAMPLE 2

1,3,8-Triaza-3-(2,3-epoxypropyl)-7,7,9,9-tetramethyl-spiro[4.5]decane-2,4-dione

To a solution of 2.4 g. of sodium hydroxide in 100 ml. of water was added 11.3 g. of 1,3,8-triaza-7,7,9,9-tetramethyl-spiro[4.5]decane-2,4-dione and the resulting mixture was stirred for a while to form the corresponding sodium salt in situ. To the resulting mixture containing the salt was added 5.5 g. of epichlorohydrin and the resulting mixture was stirred at room temperature for 6 hours.

After completion of the reaction, the crystalline substance formed in situ was recovered by filtration, washed with water and dried to give the desired product as crude crystalline substance. The substance thus obtained was dissolved in 150 ml. of benzene with heating and the resulting solution was filtered to remove insolubles. The filtrate was cooled to separate out crystalline substances, which were then recovered by filtration to give the desired product in a pure state as white crystals melting at 168.5° – 169.6°C.

Analysis for $C_{14}H_{23}N_3O_3$:
Calculated: C, 59.76%; H, 8.24%; N, 14.94%.
Found: C, 59.56%; H, 8.22%; N, 14.82%.
IR spectrum (Nujol mull):$\nu$

845 cm$^{-1}$

Following the substantially same procedure as set forth in the above Example 1, the piperidine-spiro-hydantoin compounds as listed below were prepared:

3-allyl-1,3,8-triaza-7,7,9,9-tetramethyl-spiro[4.5] decane-2,4-dione (m.p. 147° – 148°C.),
3-allyl-1,3,8-triaza-7,7,9,9-tetramethyl-spiro[4.5] decane-2,4-dithione (m.p. 182° – 183°C.),
1,3,8-triaza-3-(trans-3-bromoallyl)-7,7,9,9-tetramethylspiro[4.5]decane-2,4-dione (m.p. 183° – 184°C.),
1,3,8-triaza-3-benzyl-7,7,9,9-tetramethyl-spiro[4.5]decane-2,4-dione (m.p. 178° – 179°C.),
1,3,8-triaza-3-(p-chlorobenzyl)-7,7,9,9-tetramethyl-spiro[4.5]decane-2,4-dione (m.p. 169° – 170°C.),
1,3,8-triaza-7,7,9,9-tetramethyl-3-(p-methylbenzyl)-spiro[4.5]decane-2,4-dione (m.p. 170° – 171°C.),
1,3,8-triaza-3-(p-chloromethylbenzyl)-7,7,9,9-tetramethyl-spiro[4.5]decane-2,4-dione (m.p. 137° – 138°C.),
1,3,8-triaza-7,7,9,9-tetramethyl-3-phenethyl-spiro[4.5]decane-2,4-dione (m.p. 183° – 184°C.),
1,3,8-triaza-3-(2-hydroxyethyl)-7,7,9,9-tetramethyl-spiro[4.5]decane-2,4-dione (m.p. 188° – 189°C.),
1,3,8-triaza-3-(3-hydroxypropyl)-7,7,9,9-tetramethyl-spiro[4.5]decane-2,4-dione (m.p. 181.5° – 183°C.),
1,3,8-triaza-3-(4-hydroxybutyl)-7,7,9,9-tetramethyl-sprio[4.5]decane-2,4-dione (m.p. 113° – 114°C.),
1,3,8-triaza-3-ethoxymethyl-7,7,9,9-tetramethyl-spiro[4.5]decane-2,4-dione (m.p. 165° – 166°C.),
1,3,8-triaza-7,7,9,9-tetramethyl-3-(2-vinyloxyethyl)-spiro[4.5]decane-2,4-dione (m.p. 122° – 123°C.),
1,3,8-triaza-7,7,9,9-tetramethyl-3-(2-phenoxyethyl)-spiro[4.5]decane-2,4-dione (m.p. 157° – 158°C.),
1,3,8-triaza-7,7,9,9-tetramethyl-3-(2-methylthioethyl)-spiro[4.5]decane-2,4-dione (m.p. 146° – 147°C.),
3-(2-acetoxyethyl)-1,3,8-triaza-7,7,9,9-tetramethyl-spiro[4.5]decane-2,4-dione (m.p. 169° – 170°C.),
1,3,8-triaza-3-(4-decanoyloxybutyl)-7,7,9,9-tetramethyl-spiro[4.5]decane-2,4-dione (m.p. 99° – 100°C.),
3-(2-acryloyloxyethyl)-1,3,8-triaza-7,7,9,9-tetramethyl-spiro[4.5]decane-2,4-dione (m.p. 152.5° – 153°C.),
1,3,8-triaza-3-(2-benzoyloxyethyl)-7,7,9,9-tetramethyl-spiro[4.5]decane-2,4-dione (m.p. 166.5° – 167.5°C.),
1,3,8-triaza-7,7,9,9-tetramethyl-3-(2-m-toluoyloxyethyl)-spiro[4.5]decane-2,4-dione (m.p. 155° – 156°C.),
1,3,8-triaza-7,7,9,9-tetramethyl-3-(2-dimethylaminoethyl)-spiro[4.5]decane-2,4-dithione (m.p. 78° – 79°C.),
1,3,8-triaza-3-ethoxycarbonylmethyl-7,7,9,9-tetramethyl-spiro[4.5]decane-2,4-dione (m.p. 153° – 154°C.),
1,3,8-triaza-3-ethoxycarbonyl-7,7,9,9-tetramethyl-spiro[4.5]decane-2,4-dione (m.p. 153° – 154°C.),
3-acetyl-1,3,8-triaza-7,7,9,9-tetramethyl-spiro[4.5]-decane-2,4-dione (m.p. 285° – 287°C.),
1,3,8-triaza-7,7,9,9-tetramethyl-3-diphenoxyphosphinyl-spiro[4.5]decane-2,4-dithione (m.p. 227° – 229°C.),
1,4-bis(1,3,8-triaza-7,7,9,9-tetramethyl-2,4-dioxo-spiro[4.5]-3-decyl)-trans-2-butene (m.p. >300°C.),
2,2'-bis(1,3,8-triaza-7,7,9,9-tetramethyl-2,4-dioxo-spiro[4.5]-3-decyl)diethylether (m.p. 262° – 263°C.),
α,α'-bis(1,3,8-triaza-7,7,9,9-tetramethyl-2,4-dioxo-spiro[4.5]-3-decyl)-p-xylene (m.p. 293° – 295°C.).
bis[2-(1,3,8-triaza-7,7,9,9-tetramethyl-2,4-dioxo-spiro[4.5]-3-decyl)ethyl]adipate (m.p. 200° – 201°C.),
bis[2-(1,3,8-triaza-7,7,9,9-tetramethyl-2,4-dioxo-spiro[4.5]-3-decyl)ethyl]terephthalate (m.p. 282° – 283°C.),
tris[2-(1,3,8-triaza-7,7,9,9-tetramethyl-2,4-dioxo-spiro[4.5]-3-decyl)ethyl]trimellitate (m.p. 183° – 185°C.),
2,2',2''-tris(1,3,8-triaza-7,7,9,9-tetramethyl-2,4-dithioxo-spiro[4.5]-3-decyl)triethylphosphite (m.p. 228° – 229°C.) and
tetrakis[2-(1,3,8-triaza-7,7,9,9-tetramethyl-2,4-dioxo-spiro[4.5]-3-decyl)ethyl]pyromellitate (m.p. 288° – 291°C.)

EXAMPLE 3

Into 100 parts of polypropylene ["Noblen JHH-G", trade name, after twice recrystallizations from monochlorobenzene, available from Mitsui Toatsu Chemicals Inc., Japan] was incorporated 0.25 part of each of the stabilizing compounds of this invention as indicated below. The resulting mixture was blended and molten. The molten mixture was molded into a sheet with a thickness of 0.5 mm. under heating and pressure by a conventional technique.

As a control for comparative purpose, polypropylene sheets were formed by repeating the same procedure as described above except that no stabilizing compounds of this invention were employed.

Thereafter, all of these sheets thus prepared were tested for the "brittleness time" (which means the time, expressed in terms of hour, required until the test sheet becomes brittle) under ultraviolet irradiation at 45°C. by means of the fade-meter, "Standard Fade-Meter Type Fa-1" manufactured and sold by Toyo Rika Instruments Inc., Japan. Such a instrument is a modification of Atlas Fade-O-meter Type FDA-R (Atlas Electric Devices Co., U.S.A.) and meets the requirements prescribed in the item 3.8 of Japanese Industrial Standard "1044-L".

The results are set forth in the following Table I.

The same procedure as set forth above was repeated except that high-density polyethylene ["Hi-Zex", trade name, after twice recrystallizations from toluene, available from Mitsui Toatsu Chemicals Inc., Japan] was employed instead of the polypropylene.

The results are also given in the following Table I.

Table I.

| Compound | Brittleness time (hr.) | |
| No. | Polypropylene | High-density polyethylene |
| --- | --- | --- |
| 1 | 880 | 1540 |
| 2 | 750 | 1260 |
| 4 | 320 | 740 |
| 5 | 780 | 1420 |
| 6 | 540 | 1080 |
| 8 | 560 | 1040 |
| 9 | 620 | 1060 |
| 10 | 660 | 1140 |
| 11 | 480 | 1020 |
| 12 | 520 | 1020 |
| 13 | 520 | 980 |
| 14 | 520 | 1020 |
| 15 | 540 | 1100 |
| 17 | 880 | 1540 |
| 18 | 680 | 1100 |
| 19 | 700 | 1180 |
| 20 | 540 | 960 |
| 21 | 800 | 1560 |
| 22 | 820 | 1520 |
| 23 | 840 | 1580 |
| 24 | 720 | 1280 |
| 25 | 700 | 1260 |
| 26 | 480 | 840 |
| 27 | 880 | 2950 |
| 28 | 720 | 1220 |
| 31 | 540 | 700 |
| 33 | 760 | 1220 |
| 34 | 540 | 940 |
| 35 | 560 | 1020 |
| 36 | 420 | 880 |
| 38 | 520 | 1100 |
| 39 | 520 | 1040 |
| 42 | 580 | 1040 |
| 44 | 320 | 660 |
| 45 | 560 | 1020 |
| None | 60 | 420 |

EXAMPLE 4

Into 100 parts of polystyrene ["Styron", trade name, after recrystallization from a mixture of benzene with methanol, available from Asahi-Dow Limited, Japan] was incorporated 0.25 part of each of the stabilizing compounds of this invention as indicated below. The resulting mixture was molded at 180°C. under pressure into a plate with a thickness of 1 mm.

The plate thus formed was subjected to the exposure of ultraviolet ray irradiation in the fade meter as specified in the above Example 3 at 45°C. for 500 hours. A test piece of the treated plate was tested for color difference by means of a color-difference colorimeter according to the method prescribed in Japanese Industrial Standard "K-7103", and a change of the yellowness index of the plate was calculated according to the following equation:

$$\Delta YI = YI - YI_0$$

wherein $\Delta YI$ means a change of yellowness index, $YI$ means a yellowness index after exposure and $YI_0$ means an initial yellowness index of a test piece.

The results are summarized in the following Table II.

Table II

| Compound No. | $YI_0$ | $\Delta YI$ |
| --- | --- | --- |
| 1 | 3.5 | +1.7 |
| 5 | 4.3 | +3.8 |
| 17 | 3.5 | +1.5 |
| 21 | 4.1 | +2.1 |
| 22 | 3.7 | +2.3 |
| 23 | 3.3 | +2.8 |
| 27 | 4.5 | +1.5 |
| 28 | 4.8 | +2.9 |
| 33 | 3.9 | +3.5 |
| None | 4.8 | +17.25 |

EXAMPLE 5

Into 100 parts of ABS resin ["Kane Ace B-12", trade name, available from Kanegafuchi Spinning Co., Ltd.] was incorporated 0.5 part of each of the stabilizing compounds of this invention as indicated below, the resulting mixture was kneaded on a kneading roll at 160°C. for 6 minutes and then molded into a sheet with a thickness of about 0.5 mm.

The sheet thus formed was aged under the following aging condition and retentions of ultimate elongation and of ultimate tensile strength as well as coloration degree were determined by a conventional method.

Aging test

1. Exposure for 50 hours to the sunshine carbon apparatus prescribed in Japanese Industrial Standard JIS Z-0230 entitled "Accelerated Weathering Test of Rust Proofing Oils", Paragraph 2.

2. Aging at 190°C. for 30 minutes in a Geer's aging tester prescribed in Japanese Industrial Standard JIS-K-6301 entitled "Physical Testing Methods for Vulcanized Rubber", Paragraph 6.5.

The results are given in the following Table III.

Table III

| Compound No. | Sunshine carbon apparatus | | Geer's aging tester coloration degree |
| | Retention of ultimate elongation (%) | Retention of ultimate tensile strength (%) | |
| --- | --- | --- | --- |
| 1 | 75 | 77 | pale-brown |
| 6 | 63 | 77 | " |
| 8 | 66 | 75 | " |
| 13 | 68 | 73 | " |
| 17 | 70 | 79 | " |
| 21 | 75 | 76 | " |
| 24 | 63 | 76 | " |
| 27 | 78 | 81 | " |
| 33 | 74 | 73 | yellow |
| None | 51 | 68 | brown |

EXAMPLE 6

Into 100 parts of 6-nylon ["CM 1011", trade name, available from Toray Industries Inc., Japan] was incorporated 0.25 part of each of the stabilizing compounds of this invention as indicated below. The resulting mixture was heated and melted and then molded into a film having a thickness of about 0.1 mm. under pressure by a conventional compression molding machine. The film thus formed was aged under the following aging condition and thereafter subjected to a tensile test to determine the retentions of tensile strength and elongation by a standard method.

Aging test

1. Exposure to ultraviolet ray for 200 hours in the fade meter described in the above Example 3 at 45°C.
2. Aging at 160°C. for 2 hours in the Geer's aging tester prescribed in the above Example 5.

Table IV

| Compound No. | Fade meter Retention of ultimate elongation (%) | Fade meter Retention of ultimate tensile strength (%) | Geer's aging tester Retention of ultimate elongation (%) | Geer's aging tester Retention of ultimate tensile strength (%) |
| --- | --- | --- | --- | --- |
| 1 | 75 | 71 | 78 | 73 |
| 6 | 63 | 68 | 72 | 67 |
| 8 | 69 | 70 | 76 | 72 |
| 17 | 75 | 69 | 73 | 68 |
| 21 | 76 | 78 | 74 | 68 |
| 23 | 79 | 84 | 80 | 76 |
| 27 | 81 | 86 | 84 | 75 |
| 28 | 76 | 79 | 78 | 72 |
| None | 17 | 47 | 18 | 49 |

EXAMPLE 7

Into 100 parts of polyurethane prepared from polycaprolactone ["E-5080", trade name, available from The Nippon Elastollan Industries Ltd., Japan] was incorporated 0.5 part of each of the stabilizing compounds of this invention indicated below. The resulting mixture was heated and melted and then molded into a sheet having a thickness of about 0.5 mm. The sheet thus formed was subjected to the exposure to ultraviolet ray in the fade meter as specified in the above Example 3 at 45°C. for 15 hours and then tested for the retentions of ultimate elongation and ultimate tensile strength as in the above Example 5.

The results are given in the following Table V.

Table V

| Compound No | Retention of ultimate elongation (%) | Retention of ultimate tensile strength (%) |
| --- | --- | --- |
| 1 | 92 | 89 |
| 6 | 82 | 72 |
| 17 | 85 | 88 |
| 18 | 79 | 84 |
| 19 | 78 | 85 |
| 21 | 90 | 85 |
| 23 | 90 | 82 |
| 24 | 81 | 72 |
| 27 | 97 | 91 |
| 28 | 88 | 83 |
| 33 | 80 | 72 |
| None | 75 | 51 |

EXAMPLE 8

Into 100 parts of polyvinyl chloride ["Geon 103EP", trade name, available from The Japanese Geon Co., Ltd., Japan] were incorporated 40 parts of dioctyl phthalate and 0.1 part of each of the stabilizing compounds as indicated below. The resulting mixture was kneaded for 5 minutes on a kneading roll at 140°C. and formed into a sheet with a thickness of 1 mm.

The sheet thus formed was aged under the following aging condition to observe the discoloration of the sheet.

Aging test

1. Exposure for 200 hours to the sunshine carbon apparatus as described in the above Example 5.
2. Aging at 160°C. for 30 minutes in the Geer's aging tester as described in the above Example 5.

The results are given in the following Table VI.

Table VI

| Compound No. | Discoloration Sunshine carbon apparatus | Discoloration Geer's aging tester |
| --- | --- | --- |
| 1 | pale brown | pale reddish brown |
| 17 | '' | '' |
| 21 | '' | '' |
| 22 | '' | '' |
| 23 | '' | '' |
| 27 | '' | '' |
| None | brown | reddish brown |

EXAMPLE 9

Into 100 parts of polyester resin ["Ester-G13", trade name, available from Mitsui Toatsu Chemicals, Inc., Japan] were incorporated 1 part of benzoyl peroxide and 0.2 part of each of the stabilizing compounds as indicated below. The resulting mixture was cured by pre-heating at 60°C. for 30 minutes and then heating at 100°C. for additional 1 hour to formed into a plate with a thickness of 3 mm.

The plate thus formed was exposed to irradiation in the sunshine carbon apparatus as described in the above Example 5 for 60 hours and the change of yellowness index thereof was determined according to the method described in the above Example 4.

The results are given in the following Table VII.

Table VII

| Compound No. | $YI_0$ | $\Delta YI$ |
| --- | --- | --- |
| 1 | 2.2 | +7.0 |
| 17 | 2.3 | +7.7 |
| 21 | 2.2 | +7.2 |
| 23 | 2.2 | +8.6 |
| 24 | 2.3 | +7.9 |
| 27 | 2.2 | +5.0 |
| 28 | 2.2 | +8.8 |
| 33 | 2.3 | +8.3 |
| None | 1.8 | +13.6 |

EXAMPLE 10

Into 100 parts of polyacetal resin ["Delrin 500", trade name, available from Showa Neoprene K. K., Japan] was incorporated 0.5 part of each of the stabilizing compounds of this invention as indicated below. The resulting mixture was heated and melted at 220°C.

The resulting mixture was aged with heating at 222°C. in atmosphere for 30 minutes and then rate of reduction in decomposition was measured.

The results are given in the following Table VIII.

Table VIII

| Compound No. | Rate of reduction reduction in decomposition (%) |
| --- | --- |
| 1 | 0.38 |
| 6 | 0.43 |
| 17 | 0.33 |
| 22 | 0.37 |
| 23 | 0.35 |
| 24 | 0.44 |
| 27 | 0.31 |
| None | 0.78 |

It can be seen from the results of the above Examples 3 through 10 that the piperidine-spiro-hydantoin derivatives (I) of this invention exert a remarkably high degree of stabilizing effect against photo- and thermal-deteriorations of various synthetic polymers.

What is claimed is:

1. A synthetic polymer composition stabilized against photo and thermal deterioration wherein there is incorporated, in a sufficient amount to prevent said deterioration, a compound having the formula

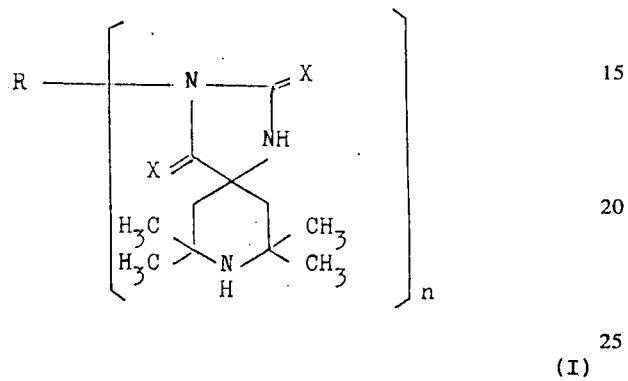

(I)

wherein X represents oxygen atom or sulfur atom; n is an integer of 1 to 4 inclusive; and R represents, when n is 1, an alkenyl group which may be substituted with halogen, an alkynyl group which may be substituted with phenyl, an aralkyl group which may be substituted with halogen, alkyl of 1 to 4 carbon atoms or halomethyl, a hydroxyalkyl group, an alkoxyalkyl group, an alkenyloxyalkyl group, an aryloxyalkyl group, an alkylthioalkyl group, and acyloxyalkyl group, an epoxyalkyl group, an N-alkyl-substituted aminoalkyl group, an alkoxycarbonylalkyl group, an aryloxycarbonylalkyl group, an alkoxycarbonyl group, $(C_2H_5O)_2$-P-,

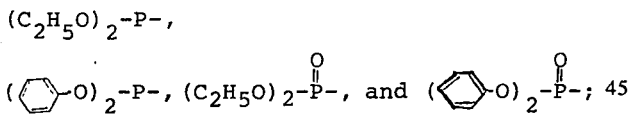

when n is 2, an alkenylene group of 4 to 18 carbon atoms, a dialkyleneether group, an aralkylene group, $-(CH_2)_2-O-CO-CO-O-(CH_2)_2-$, $-(CH_2)_2-O-CO-(CH_2)_2-CO-O-$
$(CH_2)_2-$, $-(CH_2)_2-O-CO-(CH_2)_4-CO-O-(CH_2)_2-$,
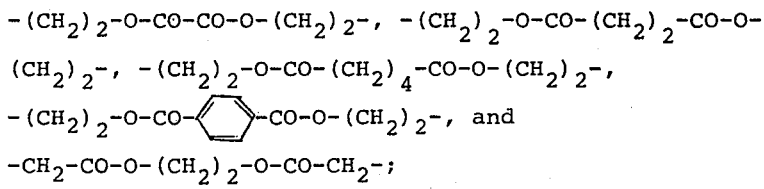, and
$-CH_2-CO-O-(CH_2)_2-O-CO-CH_2-$;

when n is 3,

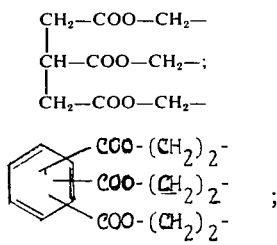

$CH_2OCOCH_2-$
$|$
$CH OCOCH_2-$
$|$
$CH_2OCOCH_2-$ or a group of the formula

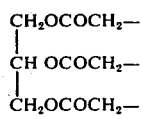

in which p is an integer of 1 to 8 inclusive and p's may be the same or different, and, when n is 4,

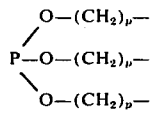

2. The synthetic polymer composition of claim 1 wherein n is 3 and R is

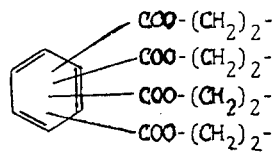

3. The synthetic polymer composition according to claim 1 wherein said compound (I) is a member selected from the compounds (I) in which n is 1 and R is an alkenyl group; an alkoxyalkyl group, an acyloxyalkyl group, an epoxyalkyl group or an alkoxycarbonylalkyl group, provided that the alkyl moiety attached directly to the N atom of a piperidinespiro-hydantoin structure has 1 to 8 carbon atoms in the substituted alkyl groups; or diphenoxyphosphinyl group.

4. The synthetic polymer composition according to claim 1 wherein said compound (I) is a member selected from the compounds (I) in which n is 1, R is allyl group; 2,3-epoxypropyl group; or an alkoxyalkyl group, an alkanoyloxyalkyl group or an alkenoyloxyalkyl group, provided that the alkyl moiety attached directly to the N atom of a piperidinespiro-hydantoin structure has 1 to 4 carbon atoms in the substituted alkyl groups and X is oxygen atom.

5. The synthetic polymer composition according to claim 1 wherein said compound (I) is incorporated in an amount of 0.01 – 5.0% by weight based upon the amount of said synthetic polymer.

6. The synthetic polymer composition according to claim 1 wherein said polymer is a homopolymer of an olefin.

7. The synthetic polymer composition according to claim 1 wherein said polymer is polypropylene or polystyrene.

8. The synthetic polymer composition according to claim 1 wherein said polymer is a copolymer of an olefin with other ethylenically unsaturated monomer.

9. The synthetic polymer composition according to claim 1 wherein said polymer is an acrylonitrile-butadiene-styrene copolymer.

10. The synthetic polymer composition according to claim 1 wherein said polymer is a polyamide having recurring amide groups as integral parts of the main polymer chain.

11. The synthetic polymer composition according to claim 1 wherein said polymer is 6-nylon.

12. The synthetic polymer composition according to claim 1 wherein said polymer is a polyurethane.

13. The synthetic polymer composition according to claim 1 wherein said polymer is a polyvinyl chloride.

14. The synthetic polymer composition according to claim 1 wherein said polymer is a polyester.

15. The synthetic polymer composition according to claim 1 wherein said polymer is a polyacetal.

16. The synthetic polymer composition according to claim 1 wherein said compound (I) is selected from the group consisting of, 3-allyl-1,3,8-triaza-7,7,9,9-tetramethyl-spiro[4.5]decane-2,4-dione, 1,3,8-triaza-3-ethoxymethyl-7,7,9,9-tetramethyl-spiro[4.5]decane-2,4-dione, 3-(2-acetoxyethyl)-1,3,8-triaza-7,7,9,9-tetramethyl-spiro[4.5]decane-2,4-dione, 1,3,8-triaza-3-(4-decanoyloxybutyl)-7,7,9,9-tetramethylspiro[4.5]decane-2,4-dione, 3-(2-acryloyloxyethyl)-1,3,8-triaza-7,7,9,9-tetramethylspiro[4.5]decane-2,4-dione and 1,3,8-triaza-3-(2,3-epoxypropyl)-7,7,9,9-tetramethylspiro[4.5]decane-2,4-dione.

\* \* \* \* \*